(12) United States Patent
Scirica et al.

(10) Patent No.: US 8,973,805 B2
(45) Date of Patent: Mar. 10, 2015

(54) SURGICAL FASTENER APPLYING APPARATUS INCLUDING A KNIFE GUARD

(75) Inventors: Paul A. Scirica, Huntington, CT (US); Eric Taylor, East Hampton, CT (US); Peter Hathaway, Lebanon, CT (US); Matthew J. Chowaniec, Middletown, CT (US)

(73) Assignee: Covidien LP, Mansfield, MA (US)

( * ) Notice: Subject to any disclaimer, the term of this patent is extended or adjusted under 35 U.S.C. 154(b) by 448 days.

(21) Appl. No.: 13/480,603

(22) Filed: May 25, 2012

(65) Prior Publication Data

US 2013/0313305 A1 Nov. 28, 2013

(51) Int. Cl.
*A61B 17/072* (2006.01)
*A61B 17/3211* (2006.01)

(52) U.S. Cl.
USPC ..................................................... 227/180.1

(58) Field of Classification Search
USPC ............... 30/2, 151, 152, 153, 154, 155, 162, 30/286, 335, 340, 329; 83/397, 398; 227/180.1, 175.1, 176.1
See application file for complete search history.

(56) References Cited

U.S. PATENT DOCUMENTS

| | | | |
|---|---|---|---|
| 5,542,594 A | 8/1996 | McKean et al. | |
| 5,908,427 A | 6/1999 | McKean et al. | |
| 5,964,774 A | 10/1999 | McKean et al. | |
| 6,010,054 A | 1/2000 | Johnson et al. | |
| 6,045,560 A | 4/2000 | McKean et al. | |
| 6,459,822 B1 | 10/2002 | Hathaway et al. | |
| 6,471,637 B1 | 10/2002 | Green et al. | |
| 6,817,508 B1 | 11/2004 | Racenet et al. | |
| 7,823,592 B2 | 11/2010 | Bettuchi et al. | |
| 7,938,307 B2 | 5/2011 | Bettuchi | |
| 2003/0130677 A1 | 7/2003 | Whitman et al. | |
| 2005/0222616 A1 | 10/2005 | Rethy et al. | |
| 2007/0023477 A1 | 2/2007 | Whitman et al. | |
| 2009/0095790 A1 | 4/2009 | Whitman et al. | |
| 2009/0101692 A1 | 4/2009 | Whitman et al. | |
| 2009/0145947 A1 | 6/2009 | Scirica et al. | |
| 2009/0179063 A1 | 7/2009 | Milliman et al. | |
| 2009/0182193 A1 | 7/2009 | Whitman et al. | |
| 2011/0040308 A1 | 2/2011 | Cabrera et al. | |

(Continued)

FOREIGN PATENT DOCUMENTS

EP 0634144 A1 1/1995
EP 2098170 A2 9/2009

(Continued)

OTHER PUBLICATIONS

European Search Report dated Aug. 30, 2013 in European Application No. 13169092. U.S. Appl. No. 13/280,898, filed Oct. 25, 2011, Kostrzewski.
U.S. Appl. No. 13/280,859, filed Oct. 25, 2011, Scirica et al.

(Continued)

*Primary Examiner* — Thanh Truong
*Assistant Examiner* — Praachi M Pathak

(57) ABSTRACT

A surgical fastener applying apparatus includes a cartridge-receiving assembly and a cartridge assembly releasably engagable therewith. The cartridge assembly includes a housing and a knife assembly having a knife translatable from an initial position to a deployed position and a knife guard pivotable between a storage position, wherein the knife guard substantially encloses the knife member, and a use position, wherein the knife member is exposed for translation through the housing. The knife guard engages to the knife member such that translation of the knife member rotates the guard to the use position.

20 Claims, 7 Drawing Sheets

(56) References Cited

U.S. PATENT DOCUMENTS

| | | |
|---|---|---|
| 2011/0082476 A1 | 4/2011 | Furnish et al. |
| 2011/0089220 A1 | 4/2011 | Ingmanson et al. |
| 2011/0121049 A1 | 5/2011 | Malinouskas et al. |
| 2011/0125138 A1 | 5/2011 | Malinouskas et al. |
| 2011/0215132 A1 | 9/2011 | Aranyi et al. |
| 2011/0253765 A1 | 10/2011 | Nicholas et al. |

FOREIGN PATENT DOCUMENTS

| | | |
|---|---|---|
| EP | 2 165 659 | 3/2010 |
| WO | WO 03/094747 | 11/2003 |
| WO | 2009039506 A1 | 3/2009 |
| WO | 2007014355 A3 | 4/2009 |

OTHER PUBLICATIONS

European Search Report for EP 10 25 2037.6 date of completion is Mar. 1, 2011 (3 pages).

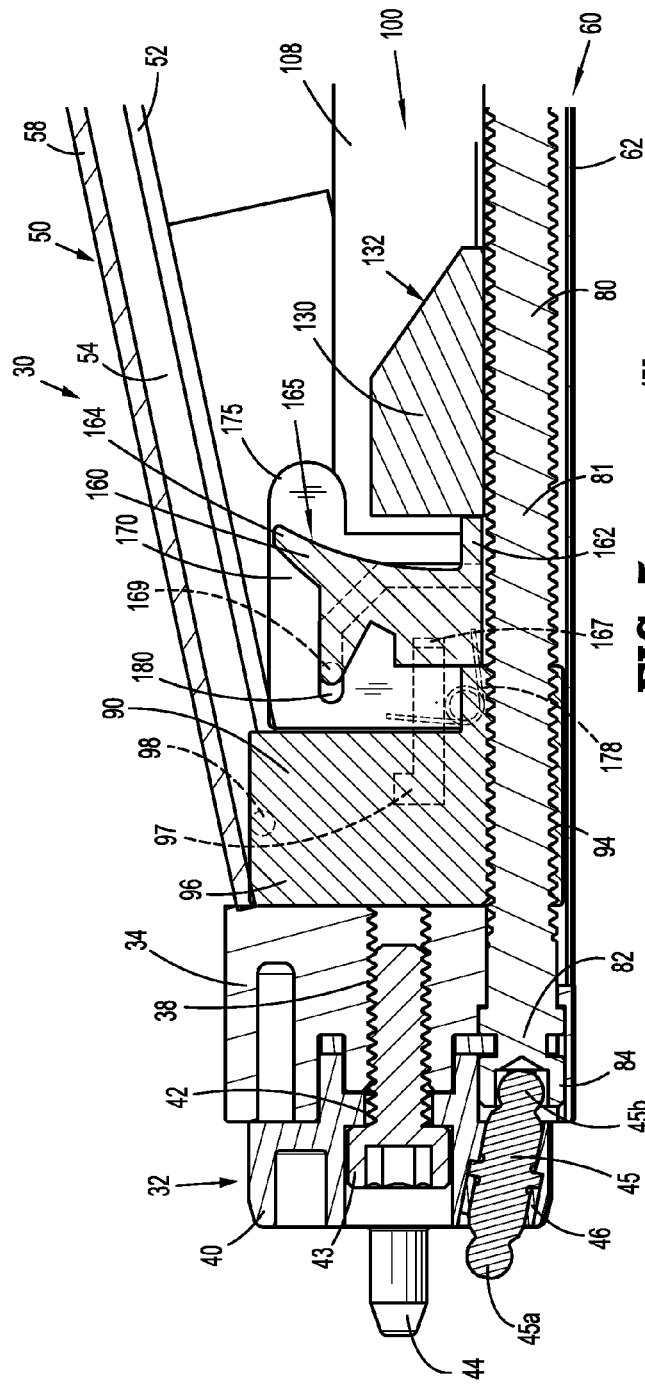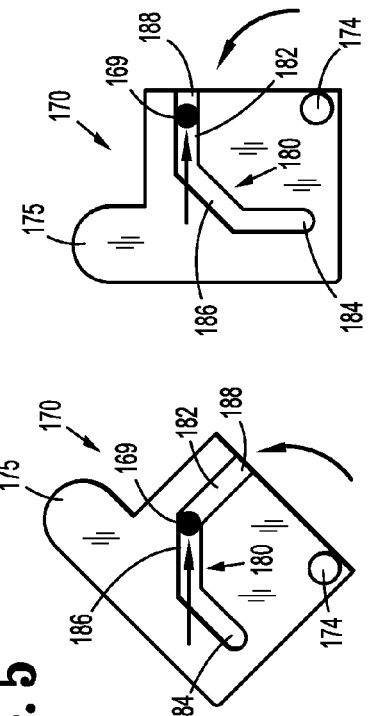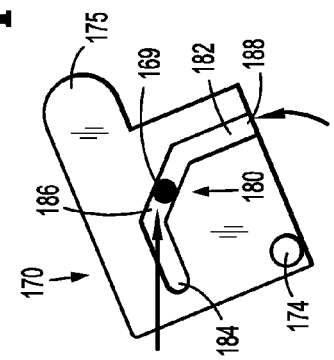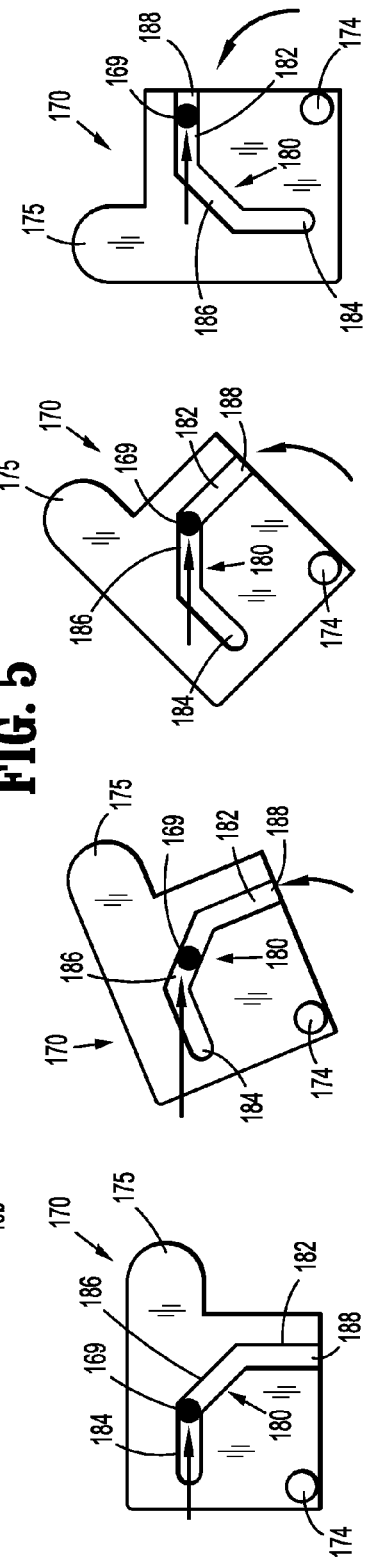

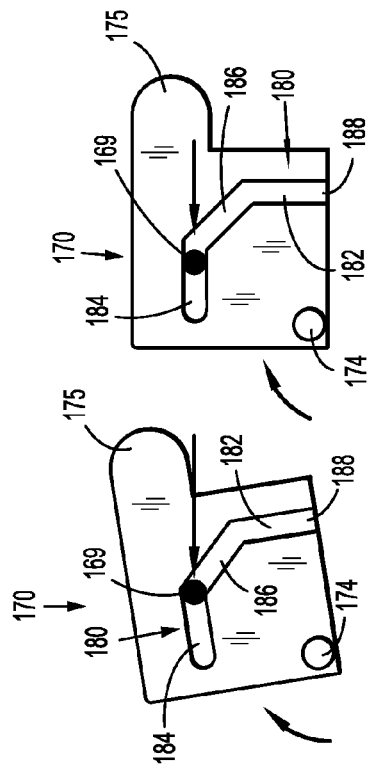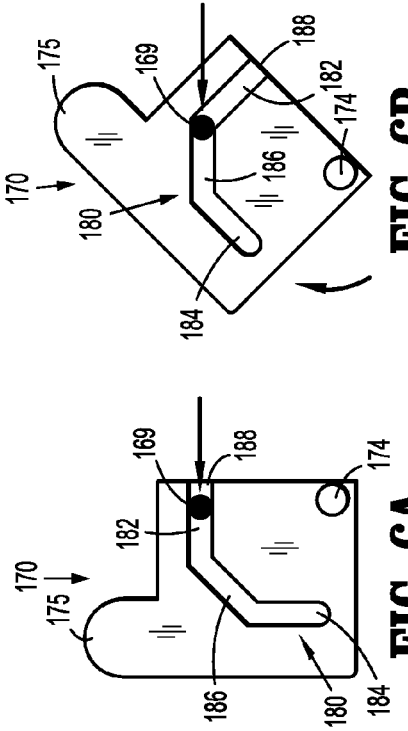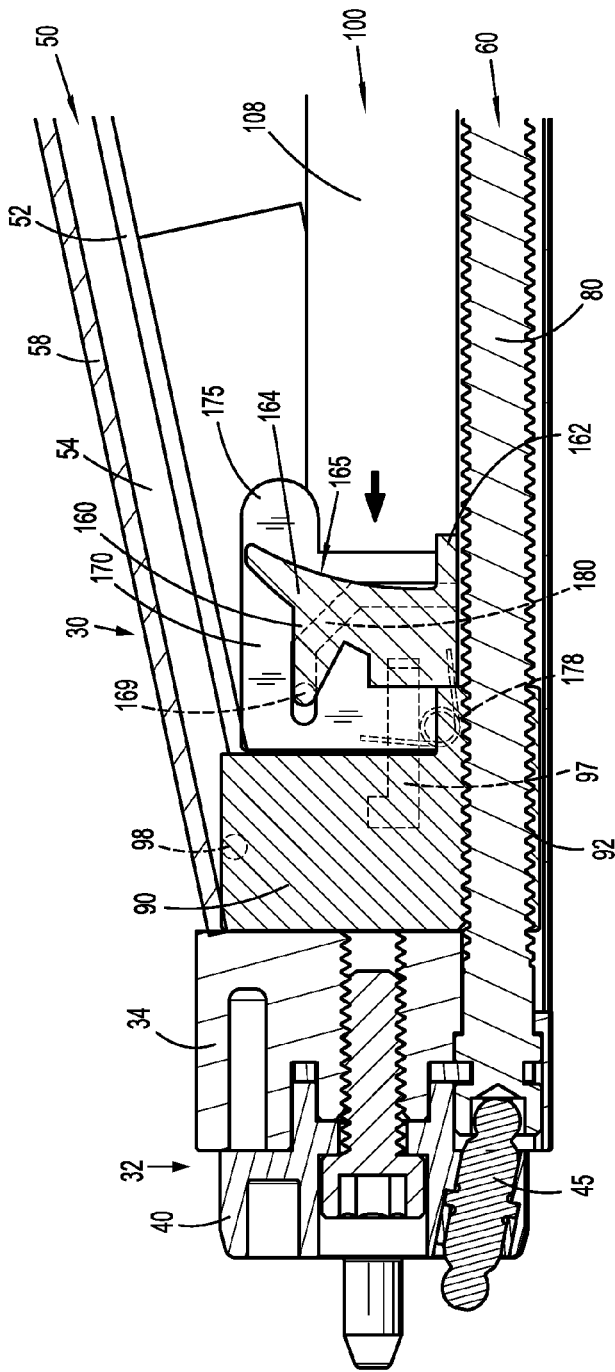

SURGICAL FASTENER APPLYING APPARATUS INCLUDING A KNIFE GUARD

BACKGROUND

1. Technical Field

The present disclosure relates to surgical fastener applying apparatus and, more particularly, to a replaceable cartridge assembly configured for use with a surgical fastener applying apparatus for clamping, stapling, and cutting tissue.

2. Background of Related Art

Surgical fastener applying apparatus, wherein tissue is first grasped or clamped between opposing jaw structures and then joined by means of surgical fasteners, are well known. In some such apparatus, a knife is provided to cut tissue that has been joined by the fasteners. The fasteners are typically in the form of surgical staples, although other surgical fasteners may also be utilized, such as, for example, clips or two part polymeric surgical fasteners.

Surgical fastener applying apparatus, as mentioned above, typically include two opposed jaw structures that are used to capture or clamp tissue therebetween. Typically, one of the jaw structures carries a cartridge assembly which houses a plurality of staples arranged in at least two lateral rows, while the other jaw structure includes an anvil which defines a surface for forming the staple legs as the staples are driven from the cartridge assembly. Where two part fasteners are used, the jaw structure which includes the anvil carries a mating part of the two part fastener, e.g. the receiver. Generally, the staple formation process is affected by the interaction between one or more longitudinally moving camming members and a series of individual staple pushers. As the camming members travel longitudinally through the cartridge assembly, the individual staple pushers are biased upwardly into a backspan of the staples supported within the cartridge assembly to sequentially eject the staples from the cartridge. Where a knife is provided, the knife follows the camming members and travels between the staple rows to cut tissue between the rows of formed staples.

In order to perform multiple clamping, stapling, and cutting operations on a single patient, surgical fastener applying apparatus have been developed that include replaceable cartridge assemblies. As such, after a first operation, the used cartridge assembly is replaced with a new cartridge assembly for a subsequent operation. As can be appreciated, it would be desirable to incorporate the knife into the replaceable cartridge assembly such that a new, sharpened knife is provided for each operation.

SUMMARY

In accordance with the present disclosure, a surgical fastener applying apparatus is provided. The surgical fastener applying apparatus includes a cartridge-receiving assembly and a cartridge assembly that is releasably engagable with the cartridge-receiving assembly. The cartridge assembly includes a cartridge housing configured to house a plurality of surgical fasteners and a knife assembly. The knife assembly includes a knife member configured to translate through the cartridge housing from an initial position to a deployed position and a knife guard pivotably coupled to the cartridge housing and movable between a storage position, wherein the knife guard substantially encloses the knife member, and a use position, wherein the knife member is exposed for translation through the cartridge housing. The knife guard engages the knife member such that translation of the knife member away from the initial position urges the knife guard to rotate from the storage position to the use position and such that translation of the knife member from the deployed position back to the storage position urges the knife guard to rotate from the use position back to the storage position.

In embodiments, the knife guard defines a cam track and the knife member includes a guard pin releasably engaged within the cam track.

In embodiments, translation of the knife member from the initial position to the deployed position urges the guard pin through the cam track to rotate the knife guard from the storage position to the use position.

In embodiments, further translation of the knife member to a further deployed position urges the guard pin to exit the cam track of the knife guard.

In embodiments, return of the knife member to the initial position urges the guard pin to enter the cam track of the knife guard and translate through the cam track of the knife guard to rotate the knife guard from the use position back to the storage position.

In embodiments, the cartridge-receiving assembly includes a drive screw and a drive member. The drive member is threadingly engaged about the drive screw such that rotation of the drive screw effects translation of the drive member.

In embodiments, the cartridge assembly further includes an actuation sled slidably disposed within the cartridge housing and configured to translate through the cartridge housing to eject the surgical fasteners from the cartridge housing.

In embodiments, translation of the drive member in a first direction urges the actuation sled and the knife member to translate through the cartridge housing in the first direction to eject the surgical fasteners from the cartridge housing and cut tissue, respectively.

In embodiments, the drive member is engagable with the knife member such that translation of the drive member in a second, opposite direction, pulls the knife member to translate in the second, opposite direction.

In embodiments, the surgical fastener applying apparatus further includes an anvil assembly movable relative to the cartridge-receiving assembly between an open position and a closed position for clamping tissue therebetween.

In embodiments, the drive member includes a cam pin configured for insertion into and translation through a corresponding slot defined within the anvil member to move the anvil assembly from the open position to the closed position upon translation of the drive member in a first direction.

In embodiments, the knife guard includes a protrusion extending therefrom such that, when the knife guard is disposed in the use position, the protrusion abuts the anvil assembly to define a minimum gap distance between the anvil assembly and the cartridge assembly.

A surgical kit is also provided in accordance with the present disclosure. The surgical kit includes a surgical fastener applying apparatus including a cartridge-receiving assembly having a drive member and an anvil assembly movable relative to the cartridge-receiving assembly between an open position and a closed position for clamping tissue therebetween. The kit further includes a plurality of cartridge assemblies. Each cartridge assembly is releasably engagable with the cartridge-receiving assembly and includes a cartridge housing configured to house a plurality of surgical fasteners, and a knife assembly. The knife assembly of each cartridge assembly includes a knife member and a knife guard. The knife member is configured to translate through the cartridge housing to cut tissue, while the knife guard pivotably coupled to the cartridge housing and movable between a storage position, wherein the knife guard substantially encloses the knife member, and a use position, wherein the knife member is exposed for translation through the cartridge housing.

In embodiments, each cartridge assembly further includes an actuation sled slidably disposed within the cartridge housing and configured to translate through the cartridge housing to eject the surgical fasteners from the cartridge housing upon translation of the drive member through the cartridge housing.

In embodiments, translation of the knife member from an initial position to a deployed position urges the knife guard to rotate from the storage position to the use position.

In embodiments, further translation of the knife member to a further deployed position urges the knife member to disengage from the knife guard.

In embodiments, return of the knife member to the initial position urges the knife guard to rotate from the use position back to the storage position.

A method of surgery is also provided in accordance with the present disclosure. The method includes providing an end effector assembly including an anvil assembly and a cartridge-receiving assembly having a drive member, engaging a first cartridge assembly with the cartridge-receiving assembly, and translating the drive member through the first cartridge assembly in a first direction to progressively approximate the anvil assembly relative to the first cartridge assembly to clamp tissue therebetween, rotate the first knife guard from a storage position to a use position, sequentially eject the first plurality of surgical fasteners from the first cartridge assembly, and translate the first knife member through the first cartridge assembly in the first direction to cut tissue between the surgical fasteners.

In embodiments, the method further includes translating the drive member through the first cartridge assembly in a second direction to translate the first knife member through the first cartridge assembly in the second direction, rotate the first knife guard from the use position back to the storage position, and progressively space-apart the anvil assembly from the first cartridge assembly. Thereafter, the first cartridge assembly is disengaged from the cartridge-receiving assembly and a second cartridge assembly is engaged with the cartridge-receiving assembly.

In embodiments, the method further includes translating the drive member through the second cartridge assembly in the first direction to progressively approximate the anvil assembly relative to the second cartridge assembly to clamp tissue therebetween, rotate the second knife guard from a storage position to a use position, sequentially eject the second plurality of surgical fasteners from the second cartridge assembly, and translate the second knife member through the second cartridge assembly in the first direction to cut tissue between the surgical fasteners.

BRIEF DESCRIPTION OF THE DRAWINGS

The above and other aspects, features, and advantages of the present disclosure will become more apparent in light of the following detailed description when taken in conjunction with the accompanying drawings wherein:

FIG. 5 is a longitudinal, cross-sectional view of a proximal end of the end effector assembly of the surgical fastener applying apparatus of FIG. 1A, wherein the drive beam, knife member, and actuation sled are in their respective initial positions and wherein the knife guard is in a storage position;

FIGS. 5A-5D are schematic illustrations showing rotation of the knife guard from the storage position to a use position;

FIGS. 6A-6D are schematic illustrations showing rotation of the knife guard from the use position back to the storage position; and FIG. 7 is a longitudinal, cross-sectional view of the proximal end of the end effector assembly of the surgical fastener applying apparatus of FIG. 1A, wherein the drive beam and knife member have been returned to their respective initial positions and wherein the knife guard has been returned to the storage position.

DETAILED DESCRIPTION

Figure 1:
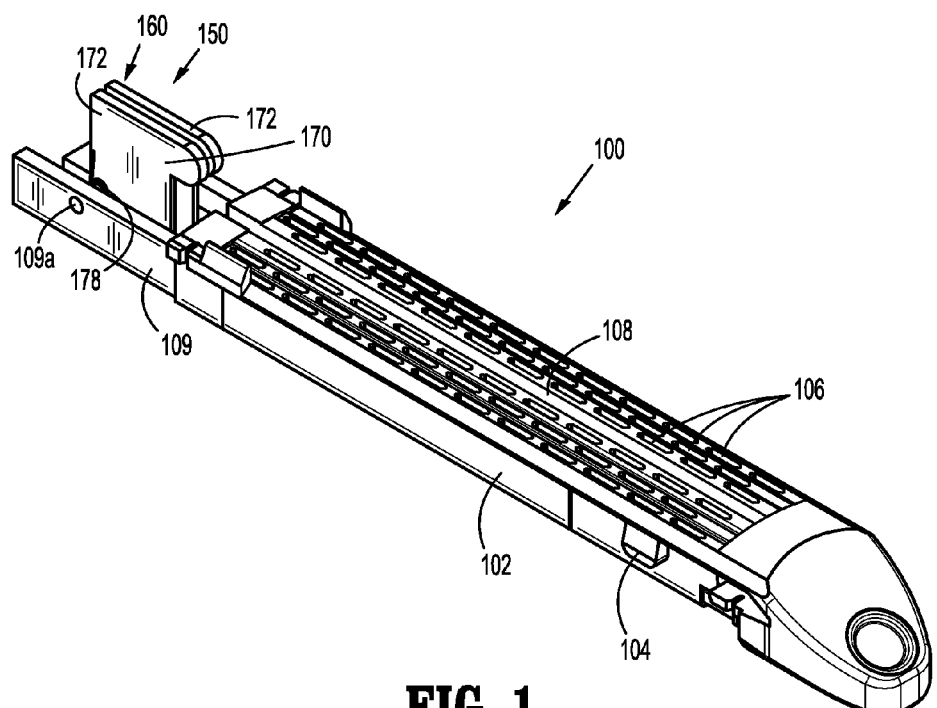
FIG. 1 is a front, perspective view of a cartridge assembly provided in accordance with the present disclosure.

Embodiments of the presently disclosed replaceable cartridge assembly and surgical fastener applying apparatus configured for use therewith are described in detail with reference to the drawings wherein like reference numerals identify similar or identical structural elements in each of the several views. As used herein, as is traditional, the term "proximal" refers to the end of the apparatus or component thereof that is closer to the user, while the term distal refers to the end of the apparatus or component thereof that is further away from the user.

Turning now to FIG. 1, a cartridge assembly provided in accordance with the present disclosure is shown generally identified by reference numeral 100. Replaceable cartridge assembly 100 is releasably engagable with an end effector assembly of a surgical fastener applying apparatus, e.g., end effector assembly 30 of surgical fastener applying apparatus 10 (see FIG. 1A), or any other suitable surgical instrument, to facilitate clamping, stapling, and cutting of tissue. Cartridge assembly 100 is configured as a replaceable, disposable component such that, after each successive clamping, stapling, and cutting operation, the used cartridge assembly 100 may be discarded and replaced with a new cartridge assembly 100 for subsequent use. Further, cartridge assembly 100 may be provided in various different configurations, e.g., including a different number, size, and/or configuration of staples, such that a desired cartridge assembly 100 may be selected for use depending on the particular procedure to be performed. Cartridge assembly 100 will be described in greater detail hereinbelow.

Figure 1A:
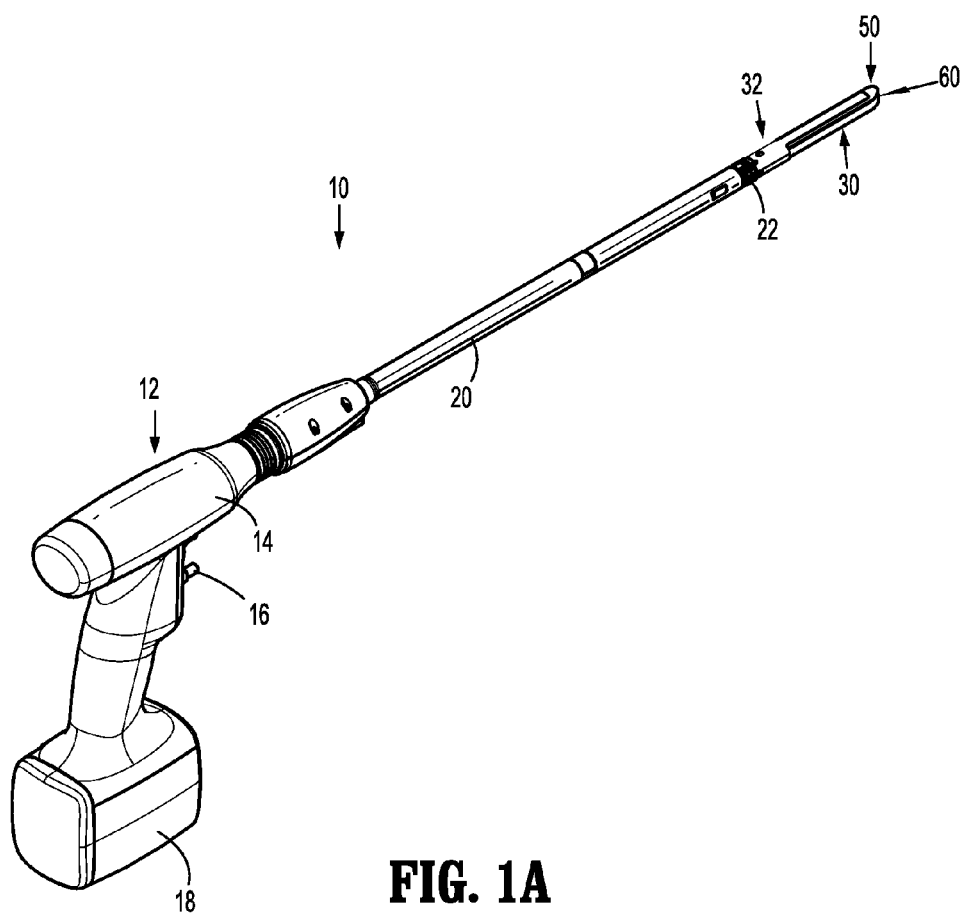
FIG. 1A is a rear, perspective view of an endoscopic, handheld surgical fastener applying apparatus provided in accordance with the present disclosure and configured for use with the cartridge assembly of FIG. 1.

With reference to FIG. 1A, an exemplary surgical fastener applying apparatus 10 configured for use with cartridge assembly 100 is shown. Surgical fastener applying apparatus 10 is configured as a handheld, endoscopic surgical fastener applying apparatus 10 and generally includes a motorized handle assembly 12 having an elongated member 20 extending distally therefrom, and an end effector assembly 30 disposed at a distal end of elongated member 20. However, other suitable surgical fastener applying apparatus, e.g., open surgical fastener applying apparatus, manually-powered surgical fastener applying apparatus, etc., are also contemplated for use with cartridge assembly 100.

Motorized handle assembly 12 of surgical fastener applying apparatus 10 includes a housing 14 and one or more actuators 16 for activating end effector assembly 30, e.g., to initiate a clamping, stapling, and cutting operation. Housing 14 houses the internal working components of motorized handle assembly 12. Motorized handle assembly 12 further includes a battery compartment 18 configured to retain a battery pack (not shown) therein for providing power to motorized handle assembly 12. An actuation shaft (not shown) extending through elongated member 20 is coupled between motorized handle assembly 12 and end effector assembly 30. More specifically, motorized handle assembly 12 is operably coupled to the actuation shaft (not shown) such that, upon actuation, e.g., upon actuation of one or more of actuators 16, the actuation shaft (not shown) is driven to actuate end effector assembly 30 to clamp, staple, and cut tissue. A detailed discussion of the construction and operation of end effector assembly 30 can be found below. A detailed discussion of the construction and operation of motorized handle assembly 12 can be found in U.S. patent application Ser. No. 12/622,827, filed on Nov. 20, 2009, and entitled "Surgical Console and Hand-held Surgical Device," the entire content of which is hereby incorporated by reference herein.

Continuing with reference to FIG. 1A, elongated member 20 includes an articulatable joint 22 disposed towards the distal end of elongated member 20. Articulatable joint 22 is operably coupled to handle assembly 12 such that end effector assembly 30 may be articulated relative to elongated member 20 by actuation of one or more of actuators 16. Alternatively or additionally, articulatable joint 22 may be articulated manually by a user, or by any other suitable mechanism provided on handle assembly 12. Articulatable joint 22 may include any suitable articulating mechanism configured to permit articulation of end effector assembly 30 relative to elongated member 20, such as, for example, gears, wires, cables, linkages, and combinations thereof.

Figure 2:
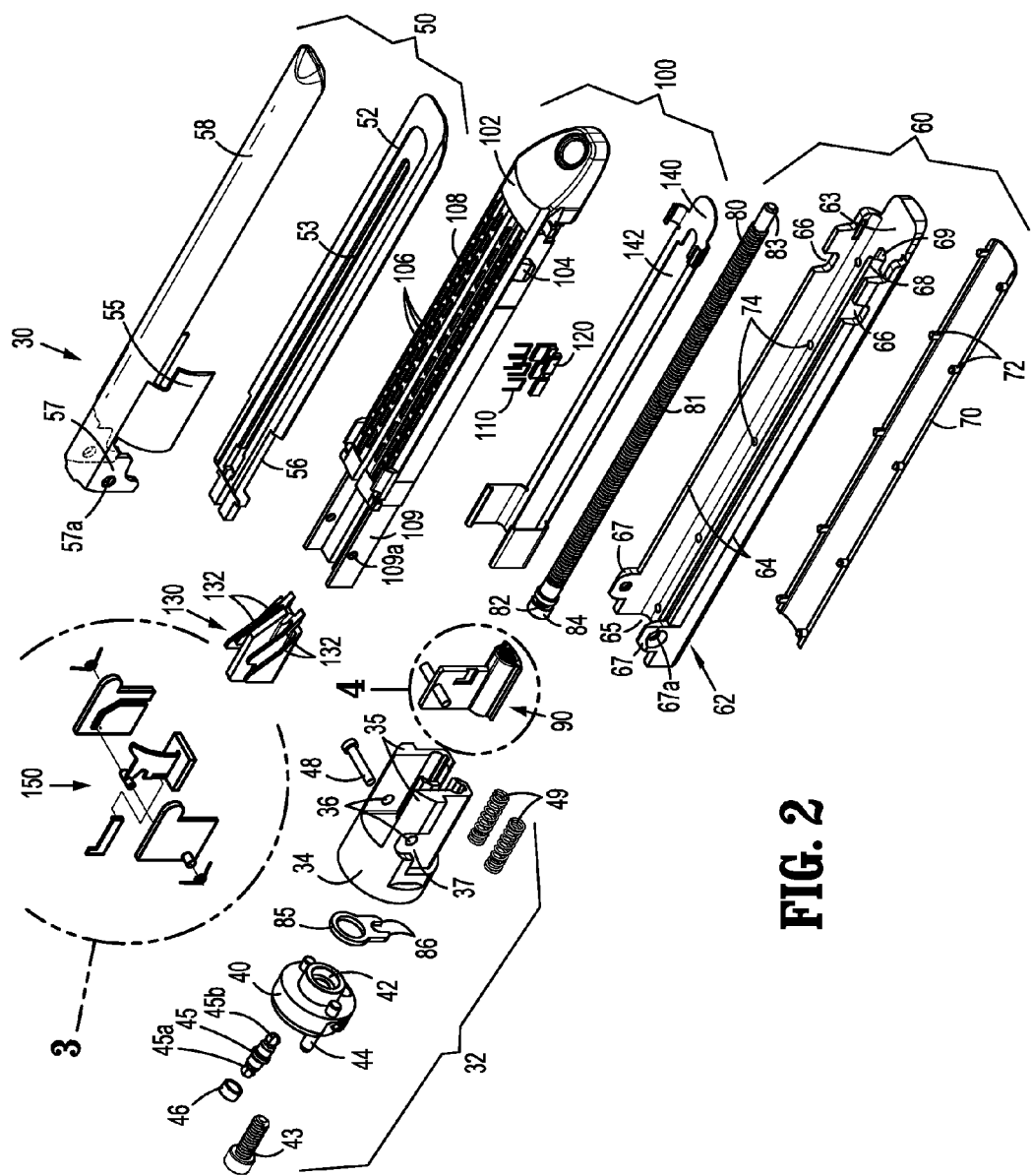
FIG. 2 is an exploded view of an end effector assembly of the surgical fastener applying apparatus of FIG. 1A including the cartridge assembly of FIG. 1.

Referring additionally to FIG. 2, as mentioned above, end effector assembly 30 is disposed at the distal end of elongated member 20. More specifically, end effector assembly 30 may be releasably engageable with elongated member 20 at the distal end thereof (as shown), e.g., via bayonet coupling or other suitable releasable engagement mechanism, or may be permanently secured at the distal end of elongated member 20. In either configuration, end effector assembly 30 includes a proximal connector assembly 32, an anvil assembly 50, and a cartridge-receiving assembly 60. Cartridge-receiving assembly 60 is configured to releasably receive cartridge assembly 100, as will be described below, and is fixedly mounted to proximal connector assembly 32 which, in turn, is mounted, e.g., releasably or fixedly mounted, at the distal end of elongated member 20. Anvil assembly 50 is pivotably coupled to proximal connector assembly 32 such that anvil assembly 50 is pivotable relative to cartridge-receiving assembly 60 and, thus, cartridge assembly 100, which is engaged within cartridge-receiving assembly 60, between an open position, wherein anvil assembly 50 and cartridge assembly 100 are spaced-apart from one another, and a closed position, wherein anvil assembly 50 is disposed in close approximation with cartridge assembly 100 to clamp tissue therebetween. However, it is also envisioned that this configuration be reversed, e.g., wherein anvil assembly 50 is mounted to proximal connector assembly 32 and cartridge-receiving assembly 60 is pivotable relative to anvil assembly 50. Alternatively, end effector assembly 30 may define a bilateral configuration, e.g., wherein both cartridge-receiving assembly 60 and anvil assembly 50 are pivotable relative to one another and proximal connector assembly 32.

Proximal connector assembly 32 generally includes a mounting member 34, a coupling member 40, and a drive shaft 45. Drive shaft 45 is disposed within mounting member 34 and is rotatably engaged therein via a bushing 46. Drive shaft 45 is oriented off-axis relative to drive screw 80 of cartridge-receiving assembly 60 such that drive shaft 45 is disposed in non-parallel orientation, e.g., at a non-zero angle, relative to drive screw 80. Drive shaft 45 includes a proximal portion 45a and a distal portion 45b. Proximal portion 45a of drive shaft 45 is configured to be engaged by the actuation shaft (not shown) that is operably coupled to and extends from handle assembly 12, while distal portion 45b of drive shaft 45 is configured to engage drive screw 80. Thus, drive shaft 45 operably couples the actuation shaft (not shown) and drive screw 80 such that actuation of the actuation shaft (not shown), e.g., via actuation one or more of actuators 16, actuates end effector assembly 30 to clamp, staple, and cut tissue.

Mounting member 34 of proximal connector assembly 32 includes a pair of spaced-apart, distally-extending extensions 35 configured to receive flanges 57 of anvil assembly 50 therebetween. Extensions 35 each define an aperture 36 therethrough that is configured for receipt of a pin 48 for pivotably coupling anvil assembly 50 to mounting member 34. Biasing members 49, e.g., coil springs, are secured within mounting member 34 and extend between extensions 35. Biasing members 49 are disposed between internal bearing surfaces (not explicitly shown) of mounting member 34 and flanges 57 of anvil assembly 50 to bias anvil assembly 50 towards the open position.

Extensions 35 each further include a depression 37 defined within the outwardly-facing surface thereof. Depressions 37 are configured to receive tabs 67 of cartridge-receiving assembly 60, while pin 48 is configured to extend through apertures 36 of extensions 35 and through apertures 67a defined within tabs 67. As such, although cartridge-receiving assembly 60 is engaged to mounting member 34 via pin 48, pivotable rotation of cartridge-receiving assembly 60 relative to mounting member 34 is inhibited due to the positioning of tabs 67 within depressions 37.

Continuing with reference to FIGS. 1-2, coupling member 40 of proximal connector assembly 32 is coupled to the proximal end of mounting member 34 and includes a threaded axial bore 42 defined therethrough. Mounting member 34 also includes a threaded axial bore 38 defined therein, which is aligned with bore 42 of coupling member 40 such that mounting member 34 and coupling member 40 may be secured to one another via a bolt 42. Coupling member 40 further includes one or more alignment shafts 44 extending proximally from coupling member 40 to facilitate alignment of end effector assembly 30 and elongated member 20 upon coupling of end effector assembly 30 and elongated member 20 to one another.

Anvil assembly 50 generally includes an anvil member 52 and an anvil cover 58. Anvil member 52 defines a fastener forming surface that generally opposes the tissue-contacting surface of cartridge assembly 100 when end effector assembly 30 is disposed in the closed position. The fastener forming surface of anvil member 52 may include a plurality of fastener pockets (not shown) configured to receive fasteners 110 and to form fasteners 110 in a closed configuration when fasteners 110 are driven from cartridge assembly 100 into the fastener pockets (not shown) of anvil member 52. Anvil member 52 further includes an elongated vertically-oriented slot 53 defined therethrough.

Anvil cover 58 is mounted about anvil member 52 and is configured to protect tissue from the moving parts of end effector assembly 30 disposed within anvil assembly 50. Anvil cover 58 includes opposed mounting wings 55 that are configured to engage respective detents 56 defined within anvil member 52. Mounting wings 55 also align anvil member 52 with cartridge assembly 100 during closure of end effector assembly 30 to facilitate proper alignment therebetween. Flanges 57 of anvil cover 58, as mentioned above, are configured for positioning between extensions 35 of mounting member 34 of proximal connector assembly 32 and each define an aperture 57a for pivotably coupling anvil assembly 50 to mounting member 34 via pin 48.

Anvil assembly 50 further includes an elongated horizontally-oriented slot 54 (FIG. 5) that is disposed in communication with elongated vertically-oriented slot 53. Horizontally-oriented slot 54 (FIG. 5) may be defined between anvil cover 58 and anvil member 52, while, as mentioned above, vertically-oriented slot 53 extends through anvil member 52. As will be described below, this configuration of slots 53, 54 (FIG. 5) allows cam pin 98 of drive beam 90 to travel between the cover 58 and anvil member 52 during firing to approximate and maintain anvil assembly 50 and cartridge assembly 100 in close approximation with one another while also allowing longitudinal translation of vertical strut 96 of drive beam 90 through and relative to anvil assembly 50.

Cartridge-receiving assembly 60 of end effector assembly 30 includes a carrier 62 and a plate cover 70. Carrier 62 includes a base 63 and first and second opposed walls 64 that cooperate to define a channel 65 extending longitudinally through carrier 62. Walls 64 of carrier 62 each define an engagement notch 66 positioned towards the distal end thereof for releasably engaging cartridge assembly 100 within channel 65. Walls 64 each further include a tab 67 disposed at the proximal end thereof for coupling carrier 62 to mounting member 34 of proximal connector assembly 32, e.g., via pin 48. More specifically, tabs 67 are configured for receipt within corresponding depressions 37 defined within mounting member 34 of proximal connector assembly 32 such that, in cooperation with pin 48, carrier 62 is fixedly engaged to mounting member 34, i.e., relative movement between carrier 62 and mounting member 34 is substantially inhibited. Base 63 of carrier 62 defines a longitudinal slot 68 having a cuff 69 defined at the distal end thereof.

Plate cover 70 of carrier 62 includes a plurality of knobs 72 configured for engagement within corresponding apertures 74 defined within carrier 62 to secure plate cover 70 to carrier 62, although carrier 62 and plate cover 70 may alternatively be engaged to one another in any other suitable fashion. Plate cover 70 is configured to protect tissue from the moving parts of end effector assembly 30 disposed within cartridge-receiving assembly 60.

With continued reference to FIGS. 1-2, end effector assembly 30 further includes an axial drive screw 80 disposed within carrier 62 of cartridge-receiving assembly 60. More specifically, axial drive screw 80 includes a threaded portion 81 disposed within longitudinal slot 68 of base 63 of carrier 62, a proximal engagement portion 82 extending proximally from cartridge-receiving assembly 60, and a distal extension 83 rotatably disposed within cuff 69 of longitudinal slot 68 of base 63 of carrier 62 to retain axial drive screw 80 within longitudinal slot 68 while also permitting rotation of axial drive screw 80 relative to carrier 62. Proximal engagement portion 82 of axial drive screw 80 includes a female connection member 84 that is configured to engage distal portion 45b of drive shaft 45. As such, and as will be described in greater detail below, axial drive screw 80 converts the rotational drive forces exerted by drive shaft 45 (which is driven by motorized handle assembly 12) into longitudinal movement of drive beam 90 (which is threadingly engaged about axial drive screw 80) for driving actuation sled 130 and knife member 160 to staple and subsequently divide tissue. In order to inhibit movement, other than rotational movement, of axial drive screw 80, a thrust plate 85 rotatably secures proximal engagement portion 82 of axial drive screw 80 between coupling member 40 and mounting member 34 of proximal connector assembly 32. More specifically, thrust plate 85 includes a pair of teeth 86 configured for positioning about proximal engagement portion 82 of axial drive screw 80, thereby inhibiting substantial lateral, longitudinal, and elevational movement of axial drive screw 80 relative to proximal connector assembly 32 and cartridge-receiving assembly 60, while permitting rotation of axial drive screw 80 about its longitudinal axis.

Figure 4:
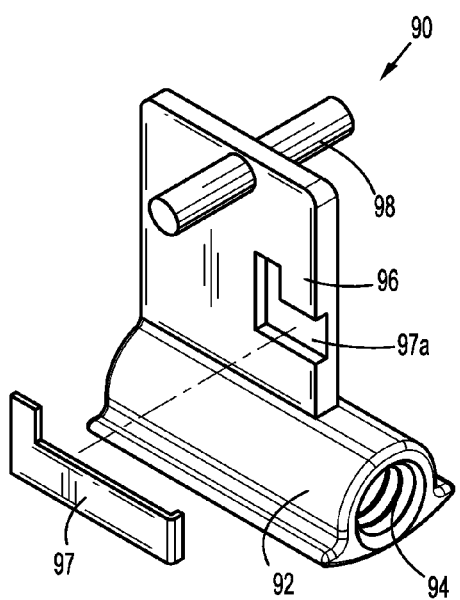
FIG. 4 is an enlarged view of the area of detail indicated as "4" in FIG. 2.

With additional reference to FIG. 4, end effector assembly 30 further includes a drive beam 90 that is operably coupled to axial drive screw 80 (and may be integrally formed therewith) and selectively translatable through and relative to cartridge assembly 100 and cartridge-receiving assembly 60. Drive beam 90 includes a retention foot 92 having a threaded bore 94 defined therethrough. Axial drive screw 80 is threadingly engaged within threaded bore 94 of drive beam 90 such that rotation of drive screw 80 effects longitudinal translation of drive beam 90 along axial drive screw 80. Drive beam 90 further includes a vertical support strut 96 extending upwardly from foot 92. Vertical support strut 96 engages a spring arm 97 within a recess 97a for releasably engaging knife member 160 to drive beam 90, as will be described in greater detail below. Drive beam 90 also includes a transverse cam pin 98 extending transversely through vertical support strut 96 towards the top end thereof. Cam pin 98 is configured for insertion into and translation through horizontally-oriented slot 54 (FIG. 5) defined within anvil assembly 50 to progressively clamp anvil assembly 50 against body tissue and cartridge assembly 100 during firing. As mentioned above, horizontally-oriented slot 54 (FIG. 5) may be defined between anvil cover 58 and anvil member 52, thus allowing cam pin 98 of drive beam 90 to travel between anvil cover 58 and anvil member 52 during firing. Vertically-oriented slot 53 (visible in FIG. 2) of anvil assembly 50, on the other hand, accommodates vertical strut 96 to permit translation of drive beam 90 relative to anvil assembly 50. Drive beam 90, as will be described below, is configured to urge knife member 160 and actuation sled 130 through cartridge assembly 100 to sequentially eject fasteners 110 from cartridge assembly 100 to staple tissue and subsequently divide tissue between the rows of fasteners 110.

Referring again to FIGS. 1-2, as mentioned above, carrier 62 is configured to releasably receive cartridge assembly 100. More specifically, cartridge assembly 100 is configured for releasable engagement within channel 65 defined by carrier 62 via the engagement of tabs 104, which extend generally downwardly and outwardly from cartridge housing 102 of cartridge assembly 100, within notches 66 of carrier 62. The positioning of cartridge assembly 100 within channel 65, e.g., between walls 64, and the engagement of tabs 104 within notches 66 function to restrict lateral, longitudinal, and elevational movement of cartridge assembly 100 within carrier 62, thus helping to ensure proper alignment of cartridge assembly 100 relative to anvil assembly 50.

Cartridge assembly 100 includes a cartridge housing 102 that is configured to house a plurality of surgical fasteners 110, a plurality of corresponding ejectors or pushers 120, and an actuation sled 130. Actuation sled 130 includes a plurality of cam wedges 132 configured such that, upon translation of actuation sled 130 through cartridge housing 102, cam wedges 132 of actuation sled 130 exert a fastener driving force on pushers 120 to urge fasteners 110 from cartridge housing 102. More specifically, a plurality of spaced-apart longitudinal slots (not shown) extend through cartridge housing to accommodate cam wedges 132 of actuation sled 130 while a plurality of vertical slots 106 communicating with the longitudinal slots (not shown) support the plurality of fasteners 110 and pushers 120 such that, as actuation sled 130 is translated through cartridge housing 102, the angled leading edges of cam wedges 132 sequentially contact pushers 120 and urge pushers 120 to translate vertically within slots 106, thereby urging fasteners 110 from slots 106. Cartridge housing 102 further defines a central longitudinal slot 108 to allow for drive beam 90 and knife member 160 to travel therethrough during actuation, and a bottom plate 140 that defines a slot 142 configured to permit passage of drive beam 90 into cartridge housing 102 upon insertion and engagement of cartridge assembly 100 within cartridge-receiving assembly 60.

Figure 3:
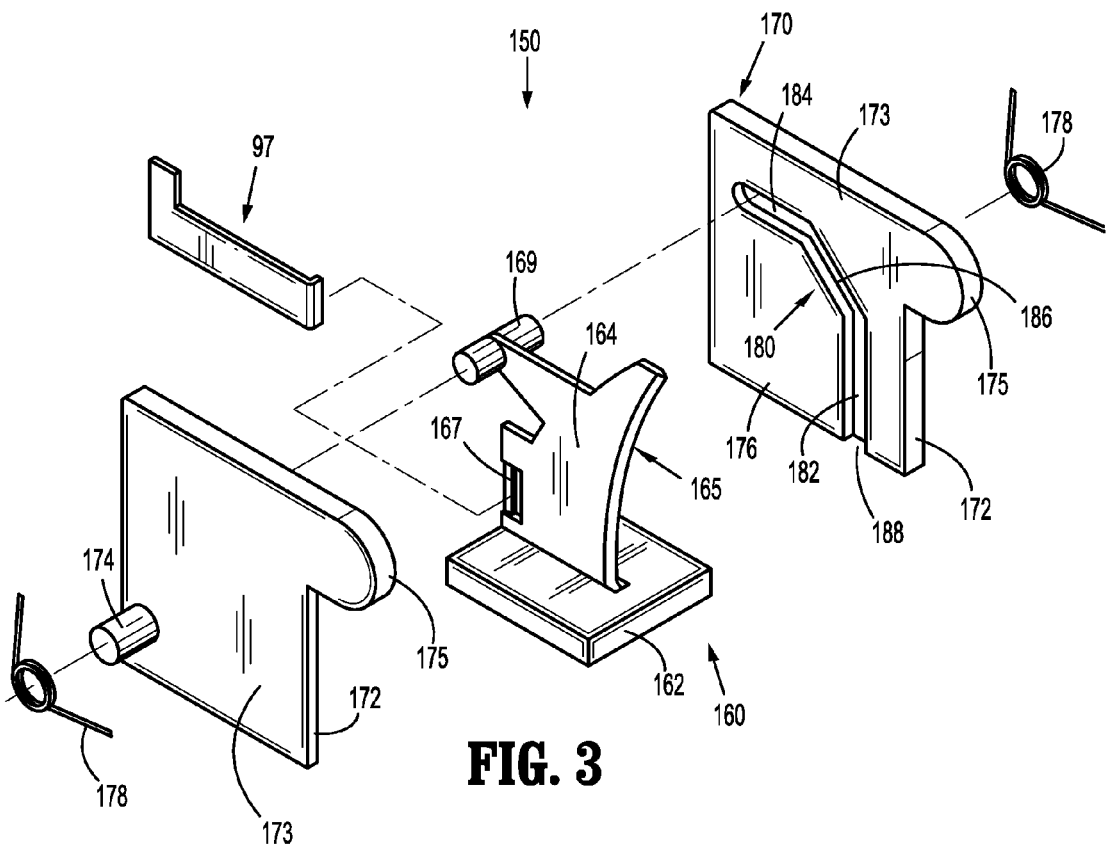
FIG. 3 is an enlarged view of the area of detail indicated as "3" in FIG. 2.

With reference to FIGS. 1-3, cartridge assembly 100 further includes a knife assembly 150 having a selectively translatable knife member 160 and a knife guard 170 pivotably mounted to a proximal extension 109 of cartridge housing 102. Knife member 160 includes a base 162 and a vertical member 164 extending generally perpendicularly from base 162. Base 162 is configured for translation through cartridge housing 102 and defines a transverse dimension that is greater than that of central longitudinal slot 108 defined within cartridge housing 102 such that base 162 of knife member 160 is retained within cartridge housing 102 during translation therethrough. Base 162 is further configured to urge actuation sled 130 distally upon distal urging of base 162 via drive beam 90 to sequentially eject fasteners 110 from cartridge assembly 100. Vertical member 164 of knife member 160 defines a distal cutting surface 165 configured to facilitate cutting of tissue upon distal translation of knife member 160, an engagement notch 167 configured to receive the free end of spring arm 97 (FIG. 4) to releasably engage knife member 160 and drive beam 90 to one another, and a transverse guard pin 169 operably associated with knife guard 170 for moving knife guard 170 between its storage and use positions.

Knife guard 170, as mentioned above, is pivotably mounted to proximal extension 109 of cartridge housing 102. More specifically, knife guard 170 is pivotable between a storage position, wherein knife guard 170 substantially encloses knife member 160, and a use position, wherein knife member 160 is exposed for translation through end effector assembly 30 to cut tissue. In certain embodiments, Knife guard 170 defines a bifurcated configuration including a pair of knife guard portions 172 that are mirror-images of one another, but embodiments having one portion or body are contemplated. Each knife guard portion 172 includes a body 173, a peg 174 extending outwardly from body 173, a protrusion 175, and a cam track 180 defined on an inwardly-facing surface 176 of body 173. Pegs 174 are configured for receipt within corresponding apertures 109a defined within proximal extension 109 of cartridge housing 102 to pivotably couple knife guard 170 to cartridge assembly 100. Biasing members 178 may be disposed about pegs 174 to bias knife guard 170 towards the storage position. Protrusions 175 function as stop members when knife guard 170 is disposed in the use position. That is, protrusions 175 abut anvil assembly 50 when end effector assembly 30 is disposed in the closed position and knife guard 170 is disposed in the use position to define a minimum gap distance between the tissue-contacting surface of cartridge assembly 100 and the fastener forming surface of anvil assembly 50.

Cam tracks 180, which are defined on the inwardly-facing surface 176 of each body 173, are configured to receive opposed ends of transverse guard pin 169 of knife member 160. In the embodiment shown, each cam track 180 includes a distal segment 182, a proximal segment 184 disposed in generally perpendicular orientation relative to distal segment 182, and an angled intermediate segment 186 interconnecting the proximal and distal segments 184, 182, respectively. However, cam tracks with other configurations are contemplated. Each distal segment 182 defines an open distal end 188 permitting the insertion of transverse guard pin 169 into and the removal of transverse guard pin 169 from cam tracks 180. As will be described in greater detail below, cam tracks 180 are configured such that, upon actuation of knife member 160, transverse guard pin 169 is translated distally through cam tracks 180 of knife guard 170 to urge knife guard 170 to rotate from the storage position to the use position and such that, upon return of knife member 160 to its initial position, transverse guard pin 169 is translated proximally through cam tracks 180 to urge knife guard 170 to rotate back to the storage position.

Figure 6:
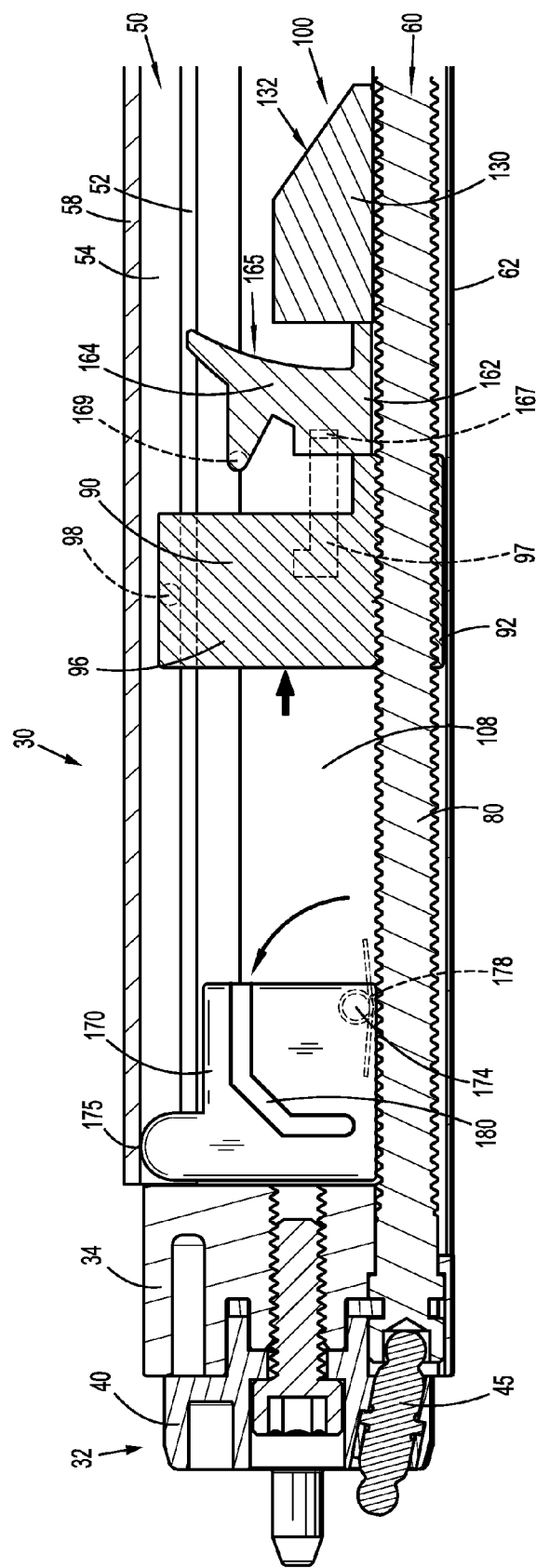
FIG. 6 is a longitudinal, cross-sectional view of the proximal end of the end effector assembly of the surgical fastener applying apparatus of FIG. 1A, showing the drive beam, knife member, and actuation sled translating distally through the end effector assembly, wherein the knife guard is in the use position.

Turning now to FIGS. 5-7, in conjunction with FIGS. 1-4, the use and operation of surgical fastener applying apparatus 10 for clamping, stapling, and cutting tissue is described. In order to assemble surgical fastener applying apparatus 10, end effector assembly 30 is engaged to elongated member 20, e.g., via bayonet coupling or other suitable releasable engagement mechanism, to operably couple the actuation shaft (not shown) of surgical fastener applying apparatus 10 and drive screw 80 to one another via drive shaft 45. Once end effector assembly 30 is engaged to elongated member 20, or prior thereto, cartridge assembly 100 is inserted into carrier 62 of cartridge-receiving assembly 60 such that cartridge assembly 100 is releasably engaged within carrier 62 via the engagement of tabs 104, which extend from cartridge housing 102, within notches 66 defined within walls 64 of carrier 62. Once end effector assembly 30 has been engaged to elongated member 20 and cartridge assembly 100 has been engaged within cartridge-receiving assembly 60, surgical fastener applying apparatus 10 is assembled and ready for use.

Initially, as shown in FIG. 5, drive beam 90 of end effector assembly 30 is disposed at the proximal end of drive screw 80, i.e., proximally of cartridge assembly 100, actuation sled 130 of cartridge assembly 100 is disposed at the proximal end of cartridge assembly 100, and knife guard 170 of knife assembly 150 is disposed in the storage position substantially enclosing knife member 160 therein. Further, in this initial condition, end effector assembly 30 is disposed in the open position, wherein anvil assembly 50 is spaced-apart from cartridge assembly 100. With end effector assembly 30 disposed in this initial condition, surgical fastener applying apparatus 10 may be maneuvered and/or manipulated into position such that tissue to be clamped, stapled, and divided is disposed between anvil member 52 and cartridge assembly 100.

Once tissue to be clamped, stapled, and divided is disposed between anvil member 52 and cartridge assembly 100, end effector assembly 30 may be actuated. In order to actuate end effector assembly 30, one or more of actuators 16 are actuated, e.g., depressed, to drive the actuation shaft (not shown) to rotate in a forward direction, thereby driving the rotation of drive shaft 45 and drive screw 80. In particular, actuation of actuator(s) 16 drives drive screw 80 to rotate in a first direction, e.g., a clockwise direction. Rotation of drive screw 80 in the first direction urges drive beam 90 to translate distally along drive screw 80. As drive beam 90 is translated distally, transverse cam pin 98 enters horizontally-oriented slot 54 defined within anvil assembly 50 such that anvil assembly 50 is progressively clamped against body tissue and cartridge assembly 100 as end effector assembly 30 is actuated further, e.g., as drive beam 90 is translated further distally. Simultaneously, or near-simultaneously, drive beam 90 is urged into contact with knife member 160 such that drive beam 90 urges knife member 160 to likewise translate distally.

With reference to FIGS. 5A-5D, in conjunction with FIGS. 1-5, as knife member 160 is translated distally under the urging of drive beam 90 and relative to knife guard 170, guard pin 169 of knife member 160 is initially translated distally through proximal segments 184 of cam tracks 180, as shown in FIG. 5A. Upon further distal translation of knife member 160 relative to knife guard 170, as shown in FIGS. 5B-5C, guard pin 169 enters angled intermediate segments 186 of cam tracks 180 wherein, due to the angled configuration of intermediate segments 186 of cam tracks 180, distal translation of guard pin 169 urges knife guard 170 to rotate from the storage position towards the use position. As shown in FIG. 5D, once guard pin 169 enters distal segments 182 of cam tracks 180, knife guard 170 has been fully rotated to the use position. Further distal translation of knife member 160 at this point translates guard pin 169 distally through distal segments 182 of cam tracks 180, ultimately exiting cam tracks 180 via the open distal ends 188 of distal segments 182.

Referring back to FIG. 5, in conjunction with FIGS. 1-4, as mentioned above, upon actuation, drive beam 90 is urged into contact with knife member 160 such that drive beam 90 urges knife member 160 to likewise translate distally. More specifically, knife member 160 is urged distally via drive beam 90 such that vertical member 164 of knife member 160 is translated through central longitudinal slot 108 of cartridge housing 102. Following behind knife member 160, vertical strut 96 of drive beam 90 is likewise translated through central longitudinal slot 108 of cartridge housing 102 and, at the same time, is translated through vertically-oriented slot 53 of anvil assembly 50. Upon entering central longitudinal slot 108 of cartridge housing 102, spring arm 97 of vertical support strut 96 of drive beam 90 is urged into engagement within engagement notch 167 of vertical member 164 of knife member 160, e.g., due to the reduced dimension of central longitudinal slot 108, to engage drive beam 90 and knife member 160 to one another. As will be described below, this engagement of drive beam 90 and knife member 160 permits knife member 160 to be retracted proximally upon proximal return of drive beam 90.

As mentioned above, during distal translation of drive beam 90, transverse cam pin 98 of drive beam 90 translates through horizontally-oriented slot 54 of anvil assembly 50 to clamp anvil assembly 50 about tissue, e.g., to maintain end effector assembly 30 in the closed position clamping tissue therebetween. However, the clamping of end effector assembly 30 is limited via protrusion 175 of knife guard 170 which, in the use position, is positioned to abut anvil assembly 50, thereby setting the minimum gap distance between the tissue-contacting surface of cartridge assembly 100 and the fastener forming surface of anvil assembly 50.

Turning now to FIG. 5, in conjunction with FIGS. 1-4, as drive screw 80 is rotated in the first direction to translate drive beam 90 distally, which, in turn, translates knife member 160 distally, base 162 of knife member 160 contact actuation sled 130 of cartridge assembly 100 and urges actuation sled 130 distally. As actuation sled 130 is urged distally, cam wedges 132 of actuation sled 130 are urged into contact with pushers 120 to sequentially eject fasteners 110 from cartridge assembly 100 and through tissue, ultimately such that fasteners 110 are formed about tissue upon contact with the fastener forming surface of anvil member 52. Knife member 160 travels slightly behind actuation sled 130 to cut tissue between the rows of fasteners 110. As can be appreciated, actuation of end effector assembly 30 may be controlled to fire greater or fewer fasteners 110 from cartridge assembly 100, depending on a particular purpose. That is, actuation sled 130, knife member 160, and drive beam 90 may be fully advanced to the distal end of drive screw 80 to fire all of the fasteners 110 from cartridge assembly 100, or may only be actuated partially to fire only a portion of the plurality of fasteners 110 disposed within cartridge assembly 100.

Referring to FIGS. 6-7, once the desired firing operation is complete, drive beam 90 and knife member 160 may be returned proximally to their initial positions via actuation one or more of actuators 16 (FIG. 1). Actuation of actuator(s) 16 (FIG. 1) drives the actuation shaft (not shown) to rotate in a reverse direction, thereby driving the rotation of drive shaft 45 and drive screw 80 in a second, opposite direction, e.g., a counter-clockwise direction. Rotation of drive screw 80 in the second direction urges drive beam 90 to translate proximally along drive screw 80. Due to the engagement between drive beam 90 and knife member 160 via spring arm 97, proximal translation of drive beam 90 likewise pulls knife member 160 proximally. However, actuation sled 130, since it is not engaged to either drive beam 90 or knife member 160, is retained in position, although it is also contemplated that actuation sled 130 be coupled to knife member 160 similarly as knife member 160 is coupled to drive beam 90, e.g., via a spring arm.

Drive beam 90 is translated proximally until transverse pin 98 of drive beam 90 is withdrawn from horizontally-oriented slot 54 of anvil assembly 50, thus allowing end effector assembly 30 to return to the open position under bias of biasing member 49. As mentioned above, proximal translation of drive beam 90 pulls knife member 160 proximally. More specifically, as shown in FIG. 6A, as knife member 160 is pulled proximally, guard pin 169 is ultimately translated into cam tracks 180 of knife guard 170 via open distal ends 188 of distal segments 182 of cam tracks 180. As shown in FIGS. 6B-6C, upon further proximal translation of knife member 160, guard pin 169 is translated proximally through distal segments 182 into angled intermediate segments 186 wherein, due to the angled configuration of intermediate segments 186 of cam tracks 180, further proximal translation of guard pin 169 urges knife guard 170 to rotate from the use position back towards the storage position. Additionally, the biasing effect of biasing members 178, which bias knife guard 170 towards the storage position, facilitates return of knife guard 170 to the storage position and/or the translation of knife member 160 back towards it initial position. Once guard pin 169 enters proximal segments 184 of cam tracks 180, as shown in FIG. 6D, knife guard 170 has been returned to the storage position, wherein knife guard 170 substantially enclose knife member 160. That is, knife member 160 is returned to its initial position, as shown in FIG. 7, wherein guard pin 169 is disposed towards the proximal ends of proximal segments 184 of cam tracks 180.

Upon drive beam 90 returning proximally such that vertical strut 96 of drive beam 90 is withdrawn from central longitudinal slot 108 of cartridge housing 102, spring arm 97 is no longer urged into engagement with knife member 160 via knife guard 170 or cartridge housing 102 and, thus, is permitted to return outwardly under bias outwardly to disengage drive beam 90 and knife member 160 from one another. With end effector assembly 30 once again disposed in its initial condition, the used cartridge assembly 100 may be disengaged from cartridge-receiving assembly 60 of end effector assembly 30 and a new cartridge assembly 100 may be engaged within cartridge-receiving assembly 60 for subsequent clamping, stapling, and cutting operations. Thus, the knife member 160 is discarded with the used staple cartridge and the fresh, unfired cartridge assembly has a new knife.

It will be understood that various modifications may be made to the embodiments of the surgical fastener applying apparatus disclosed herein. Therefore, the above description should not be construed as limiting, but merely as exemplifications of embodiments. Those skilled in the art will envision other modifications within the scope and spirit of the present disclosure.

What is claimed is:

1. A surgical fastener applying apparatus, comprising:
   a cartridge-receiving assembly;
   a cartridge assembly releasably engagable with the cartridge-receiving assembly, the cartridge assembly including:
      a cartridge housing configured to house a plurality of surgical fasteners; and
      a knife assembly, the knife assembly including:
         a knife member configured to translate through the cartridge housing from an initial position to a deployed position; and
         a knife guard pivotably coupled to the cartridge housing and movable between a storage position, wherein the knife guard substantially encloses the knife member, and a use position, wherein the knife member is exposed for translation through the cartridge housing, the knife guard interacting with the knife member such that translation of the knife member away from the initial position urges the knife guard to rotate from the storage position to the use position and such that translation of the knife member back to the storage position urges the knife guard to rotate from the use position back to the storage position.

2. The surgical fastener applying apparatus according to claim 1, wherein the knife guard defines a cam track and wherein the knife member includes a guard pin releasably engaged within the cam track.

3. The surgical fastener applying apparatus according to claim 2, wherein translation of the knife member from the initial position to the deployed position urges the guard pin through the cam track to rotate the knife guard from the storage position to the use position.

4. The surgical fastener applying apparatus according to claim 3, wherein further translation of the knife member to a further deployed position urges the guard pin to exit the cam track of the knife guard.

5. The surgical fastener applying apparatus according to claim 4, wherein return of the knife member to the initial position urges the guard pin to enter the cam track of the knife guard and translate through the cam track of the knife guard to rotate the knife guard from the use position back to the storage position.

6. The surgical fastener applying apparatus according to claim 2, wherein the cartridge-receiving assembly includes a drive screw and a drive beam, the drive beam threadingly engaged about the drive screw such that rotation of the drive screw effects translation of the drive beam.

7. The surgical fastener applying apparatus according to claim 6, wherein the cartridge assembly further includes an actuation sled slidably disposed within the cartridge housing and configured to translate through the cartridge housing to eject the surgical fasteners from the cartridge housing.

8. The surgical fastener applying apparatus according to claim 7, wherein translation of the drive beam in a first direction urges the actuation sled and the knife member to translate through the cartridge housing in the first direction to eject the surgical fasteners from the cartridge housing and cut tissue, respectively.

9. The surgical fastener applying apparatus according to claim 8, wherein the drive beam is engagable with the knife member such that translation of the drive beam in a second, opposite direction, pulls the knife member to translate in the second, opposite direction.

10. The surgical fastener applying apparatus according to claim 6, further comprising an anvil assembly movable relative to the cartridge-receiving assembly between an open position and a closed position for clamping tissue therebetween.

11. The surgical fastener applying apparatus according to claim 10, wherein the drive beam includes a cam pin configured for insertion into and translation through a corresponding slot defined within the anvil member to move the anvil assembly from the open position to the closed position upon translation of the drive beam in a first direction.

12. The surgical fastener applying apparatus according to claim 10, wherein the knife guard includes a protrusion extending therefrom and wherein, when the knife guard is disposed in the use position, the protrusion abuts the anvil assembly to define a minimum gap distance between the anvil assembly and the cartridge assembly.

13. A surgical kit, comprising:
    a surgical fastener applying apparatus, the surgical fastener applying apparatus including:
       a cartridge-receiving assembly including a drive beam; and
       an anvil assembly movable relative to the cartridge-receiving assembly between an open position and a closed position for clamping tissue therebetween; and
    a plurality of cartridge assemblies, each cartridge assembly releasably engagable with the cartridge-receiving assembly, each cartridge assembly including:
       a cartridge housing configured to house a plurality of surgical fasteners; and
       a knife assembly including a knife member and a knife guard, the knife member configured to translate through the cartridge housing to cut tissue, the knife guard pivotably coupled to the cartridge housing and movable between a storage position, wherein the knife guard substantially encloses the knife member, and a use position, wherein the knife member is exposed for translation through the cartridge housing.

14. The surgical kit according to claim 13, wherein each cartridge assembly further includes an actuation sled slidably disposed within the cartridge housing and configured to translate through the cartridge housing to eject the surgical fasteners from the cartridge housing upon translation of the drive beam through the cartridge housing.

15. The surgical kit according to claim 13, wherein translation of the knife member from an initial position to a deployed position urges the knife guard to rotate from the storage position to the use position.

16. The surgical kit according to claim 15, wherein further translation of the knife member to a further deployed position urges the knife member to disengage from the knife guard.

17. The surgical kit according to claim 16, wherein return of the knife member to the initial position urges the knife guard to rotate from the use position back to the storage position.

18. A method of surgery, comprising the steps of:
providing an end effector assembly including an anvil assembly and a cartridge-receiving assembly having a drive beam;
engaging a first cartridge assembly with the cartridge-receiving assembly, the first cartridge assembly housing a first plurality of surgical fasteners and including a first knife assembly having a first knife member and a first knife guard; and
translating the drive beam through the first cartridge assembly in a first direction to progressively approximate the anvil assembly relative to the first cartridge assembly to clamp tissue therebetween, rotate the first knife guard from a storage position to a use position, sequentially eject the first plurality of surgical fasteners from the first cartridge assembly, and translate the first knife member through the first cartridge assembly in the first direction to cut tissue between the surgical fasteners.

19. The method according to claim 18, further comprising the steps of:
translating the drive beam through the first cartridge assembly in a second direction to translate the first knife member through the first cartridge assembly in the second direction, rotate the first knife guard from the use position back to the storage position, and progressively space-apart the anvil assembly from the first cartridge assembly;
disengaging the first cartridge assembly from the cartridge-receiving assembly; and
engaging a second cartridge assembly with the cartridge-receiving assembly, the second cartridge assembly housing a second plurality of surgical fasteners and including a second knife assembly having a second knife member and a second knife guard.

20. The method according to claim 19, further comprising the steps of:
translating the drive beam through the second cartridge assembly in the first direction to progressively approximate the anvil assembly relative to the second cartridge assembly to clamp tissue therebetween, rotate the second knife guard from a storage position to a use position, sequentially eject the second plurality of surgical fasteners from the second cartridge assembly, and translate the second knife member through the second cartridge assembly in the first direction to cut tissue between the surgical fasteners.

* * * * *